United States Patent [19]

Goulding et al.

[11] Patent Number: 5,328,644

[45] Date of Patent: Jul. 12, 1994

[54] NEMATIC LIQUID CRYSTAL MIXTURES AND FLUORINATED CHLOROTERPHENYLS

[75] Inventors: Mark Goulding, Poole; Simon Greenfield; David Coates, both of Dorset; Robert Clemitson, Poole, all of Great Britain

[73] Assignee: Merck Patent Gesellschaft, Darmstadt, Fed. Rep. of Germany

[21] Appl. No.: 973,914

[22] Filed: Nov. 12, 1992

[51] Int. Cl.⁵ .................. C09K 19/12; C09K 19/52; C07C 25/00

[52] U.S. Cl. ..................... 252/299.66; 252/299.01; 570/127; 570/182

[58] Field of Search ............. 252/299.01, 299.64, 252/299.65, 299.66; 570/127, 182

[56] References Cited

U.S. PATENT DOCUMENTS 5,198,149 3/1993 Reiffenrath et al. ........... 252/299.61
5,213,710 5/1993 Reiffenrath et al. ........... 252/299.63

FOREIGN PATENT DOCUMENTS 439089 1/1991 European Pat. Off.
WO90/09420 3/1990 PCT Int'l Appl.
WO90/15113 5/1990 PCT Int'l Appl.
WO91/13850 3/1991 PCT Int'l Appl.

OTHER PUBLICATIONS

U.S. Patent Application Ser. No. 07/469,499, filed Mar. 21, 1990.

*Primary Examiner*—Shean Wu
*Attorney, Agent, or Firm*—Millen, White, Zelano & Branigan

[57] ABSTRACT

Disclosed is a nematic liquid crystal mixture having a positive dielectric anisotropy $\Delta\epsilon$ of at least +4 and a birefringence $\Delta n$ of at least 0.18, said mixture comprising at least one fluorinated chloroterphenyl compound of formula I R—E—Cl       I wherein
R is an alkyl or alkenyl radical having up to 15 C atoms, said radical being unsubstituted or substituted by halogen, one or more $CH_2$ groups in the radical optionally being replaced, in each case independently of one another, by —O—,

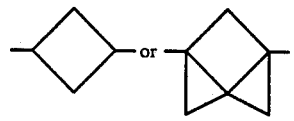

in such a manner that oxygen atoms are not linked directly to one another, and is

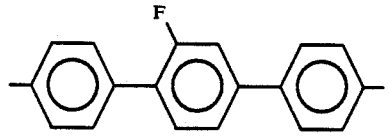

or the mirror image thereof, and wherein the benzene rings can be optionally further substituted by fluorine.

10 Claims, No Drawings

NEMATIC LIQUID CRYSTAL MIXTURES AND FLUORINATED CHLOROTERPHENYLS

BACKGROUND OF THE INVENTION

The invention relates to nematic liquid crystal mixtures having a positive dielectric anisotropy and an optical birefringence of at least 0.18, said mixtures being useful for an active matrix liquid crystal display (AMD) being operated in the second or a higher transmission minimum of the Gooch-Tarry curve and to novel fluorinated chloroterphenyls.

Active matrix displays (AMD) are highly favored for commercially interesting displays with a high information content. Such AMDs are used for TV application (e.g. for projection systems) and also for displays for e.g. laptops, automobiles and airplanes.

AMDs have non-linear electrical switching elements which are integrated at each picture element. As non-linear driving elements thin film transistors (TFT) [Okubo, U., et al., 1982, SID 82 Digest, pp. 40-41] or diodes (e.g.: metal insulator metal: MIM) [Niwa, K., et al., 1984, SID 84, Digest, pp. 304-307] can be applied. These non-linear driving elements allow use of an electro-optical effect with a rather flat electro-optical characteristic if a good viewing angle characteristic can be obtained. So a TN-type LC cell [Schadt, M. and Helfrich, W., 1971, Appl. Phys. Lett., 18, 127] with a twist angle of 90° can be used. To provide good contrast over a wide viewing angle, operation in the first minimum of transmission [Pohl, L., Eidenschink, R., Pino, F. del., and Weber, G., 1980, German Pat., DBP 30 22 818, and 1981, U.S. Pat. No. 4,398,803; Pohl, L. Weber, G., Eidenschink, R., Baur, G., and Fehrenbach, W., 1981, Appl. Phys. Lett., 38, 497; Weber, G., Finkenzeller, U., Geelhaar, T., Plach, H. J., Rieger, B., and Pohl, L., 1988, Int. Syrup. on Liq. Cryst., Freiburg, Liq. Crys. 1989, Vol. 5 pp. 1381-1388] is required. These AMDs are very well suited for TV applications and consequently are of high commercial interest. For these applications some physical properties of the liquid crystals become more important than for passive TN displays. Some of the decisive properties for the performance of an AMD are resistivity and stability of the liquid crystal [Togashi, S., Sekiguchi, K., Tanabe, H., Yamamoto, E., Sorimachi, K., Kajima, E., Watanabe, H., Shimuzu, H., Proc. Eurodisplay 84, September, 1984: A 210-288 Matrix LCD Controlled by Double Stage Diode Rings, p. 144 ff, Paris; Stromer, M., Proc. Eurodisplay 84, September 1984: Design of Thin Film Transistors for Matrix Addressing of Television Liquid Crystal Displays, p. 145 ff, Paris]. A problem often encountered is the adverse influence of UV-illumination on the resistivity and therefore on the general performance of the liquid crystal mixture in the display.

In an AMD the non-linear switching elements are addressed in a multiplex scheme, and charge the electrodes of a pixel in the limited time they are active. Then they become inactive until they are addressed again in the next cycle. Consequently the change of the voltage on an activated (charged) pixel is a nondesired but a very decisive feature of such a display. The discharge of a pixel is determined by two factors. These are the capacity of the pixel element including liquid crystal and resistivity of the dielectric material between the electrodes, namely the liquid crystal. The characteristic time constant of the decay of the voltage at a pixel (RC-time) has to be significantly bigger than the time between two adressing cycles ($t_{adr.}$). A parameter frequently used to describe the performance of an AMD is the voltage holding ratio HR of a picture element:

$$HR = \frac{V(t_o) + V(t_o + t_{adr.})}{2 V(t_o)}$$

As the voltage at a pixel decays exponentially an increase of the holding ratio necessitates liquid crystal materials with exceptionally high resistivities.

There are several points of importance for the resistivity of the liquid crystal inside a display, e.g. orientation layers, curing condition of the orientation material. But by no means less important are the electrical properties of the liquid crystal used. Especially the resistivity of the liquid crystal in the display determines the magnitude of the voltage drop at the pixel.

Earlier investigations with low-$\Delta n$ materials have shown, that the requirements with regard to resistivity and UV-stability and temperature dependence of the resistivity for TFT-applications cannot be met with materials containing cyano moieties as terminal groups. Non-cyano materials containing halogenated terminal groups can show for better resistivity values and UV-stability as well as superior viscosity values than conventionally used cyano materials. However, in general these non-cyano materials unfortunately show a strong tendency towards forming crystalline and/or smectic phases, especially at low temperatures. Also the clearing points and the dielectric anisotropy values of non-cyano materials with halogenated terminal groups are much lower.

Modern commercial mixtures have to operate over a wide temperature range; therefore, crystallization or formation of smectic phases at low temperatures has to be excluded. Good solubility is one of the most important preconditions for the usability of liquid crystalline materials in the development of nematic mixtures. Compounds with high melting temperatures or a tendency to form smectic phases are for this reason not suitable.

By very careful selection of the components and an appropriate mixture design it was possible to find low birefringence non-cyano mixtures having a broad nematic temperature range for first minimum application [B. Rieger et al., Proc. 18. Freiburger Arbeitstagung Flussigkristalle, Freiburg 1989, 16 (1989)]. Non-cyano materials with high birefringence, which are essential for the mixture concept of this invention unfortunately show in many cases even more unfavorable properties such as high melting points and/or strongly smectogenic behavior than similar materials with lower birefringence:

| No. | Chemical structure | $\Delta n$ | Mesophases (°C.) |
|-----|-------------------|------------|------------------|
| 1   | 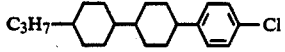 C$_3$H$_7$—⟨⟩—⟨⟩—⟨⟩—Cl | 0.126 | K 70 S 79 N 193 I |
| 2   | 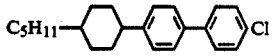 C$_5$H$_{11}$—⟨⟩—⟨⟩—⟨⟩—Cl | 0.199 | K 142 N 192 I |
| 3   | 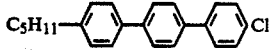 C$_5$H$_{11}$—⟨⟩—⟨⟩—⟨⟩—Cl | n.m. | K 105 S 245 I |

Mixtures of the state of the art with a birefringence suited for operation in the second or a higher transmission minimum of the Gooch-Tarry curve are not acceptable for active matrix application.

There is thus still a great need for liquid-crystal composition having a high resistivity and other suitable material properties for use in AMDs.

The chloroterphenyls No. 3 as shown above are known from JP 60-056 932-A. As outlined above these compounds do not allow meeting the severe specifications from the electronic industry, especially in view of their limited solubility in other LC materials, their high melting points and their pronounced smectogenity. Accordingly there is also a need in the art for improved non-cyano high birefringence LC compounds.

SUMMARY OF THE INVENTION

The invention has for one of its objectives to provide a nematic liquid crystal mixture having a positive dielectric anisotropy $\Delta\epsilon$ of at least +4 and a birefringence $\Delta n$ of at least 0.18, characterized in that the mixture comprises one or more fluorinated chloroterphenyls having the formula I

wherein
R is an alkyl or alkenyl radical having up to 15 C atoms, these radicals being unsubstituted or substituted by halogen, preferably 1-3 times per carbon atom, and preferably perhalo, e.g., perfluoro, it also being possible for one or more CH$_2$ groups in these radicals to be replaced, in each case independently one of another, by —O—,

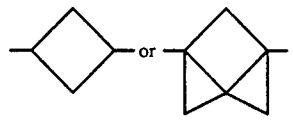

in such a manner that oxygen atoms are not linked directly to one another, and
E is

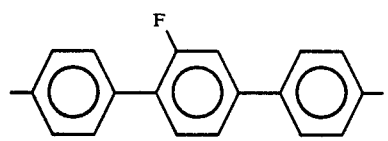

or the mirror image thereof, and wherein the benzene rings can be optionally further substituted by fluorine, e.g., 2, 3, 5 and/or 6-positions.

The invention has also as an object to provide a matrix liquid crystal display with high temperature and UV-stability containing
two plane parallel support plates which together with a frame form a cell of the thickness d,
integrated non-linear elements for switching individual picture elements on the support plates, and
a nematic liquid crystal mixture which is present in the cell, has a positive dielectric anisotropy and a birefringence $\Delta n$,
the display being operated in the second or a higher transmission minimum of the Gooch-Tarry curve by appropriate selection of d $\Delta n$, characterized in that the quotient of the voltage holding ratio HR$_{20}$ after 20 hours exposure to UV-light (280–400 nm, 12 mW/cm$^2$) and Hr$_0$ before exposure to UV-light is larger or equal to 98% and also liquid crystal compositions with a very high resistivity which meet also the other demands.

A further objective of the present invention was to provide improved fluorinated chloroterphenyls of the formula Ia

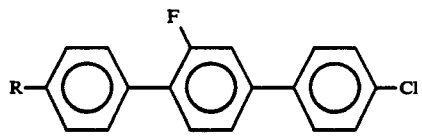

wherein
R is an alkyl or alkenyl radical having up to 15 C atoms, these radicals being unsubstituted or substituted by halogen, it also being possible for one or more CH$_2$ groups in these radicals to be replaced, in each case independently of one another by —O—,

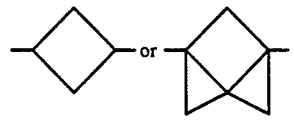

in such a manner that oxygen atoms are not linked directly to one another, and wherein the benzene rings can be independently of one another further substituted by fluorine.

It has now been found that such values for the HR are even possible for mixtures with higher birefringence by using laterally fluorinated and/or ethyl-linked non-cyano materials. Very high RC time values can be obtained in AMDs. These mixtures also show a reduced viscosity and allow short switching times at reasonable threshold voltages, The thickness of the AMDs is preferably in the range of 3 to 10 $\mu$m. Especially preferred is the range from 3 to 7 $\mu$m.

The following preferred embodiments concern the nematic liquid crystal mixture which is present in the AMD:

The birefringence $\Delta n$ of the nematic liquid crystal mixture is 0.18 to 0.29 preferably 0.20 to 0.25.

The dielectric anisotropy of the nematic liquid crystal mixture is at least +4.0.

The liquid crystal mixture, in addition to compounds of formula I, preferably comprises one or more compounds of formula II

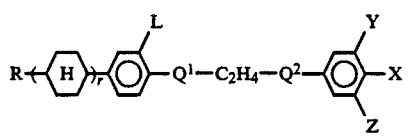

wherein
R is an alkyl or alkenyl radical having up to 15 C atoms, these radicals being unsubstituted or substituted by halogen, it also being possible for one or more CH$_2$ groups in these radicals to be replaced, in each case independently of one another, by —O—,

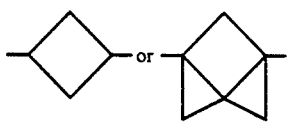

in such a manner that oxygen atoms are not linked directly to one another, r is 0 or 1, X is F, Cl, CF$_3$, OCF$_3$ or OCHF$_2$, and L, Y and Z are each H or F, and one of Q$^1$ and Q$^2$ is 1,4-phenylene or 3-fluoro-1,4-phenylene and the other residue is a single bond.

The liquid crystal mixture preferably comprises one or more compounds of the formula III

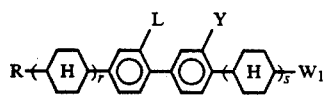    III wherein

R is an alkyl or alkenyl radical having up to 15 C atoms, these radicals being unsubstituted or substituted by halogen, it also being possible for one or more CH$_2$ groups in these radicals to be replaced, in each case independently of one another, by —O—,

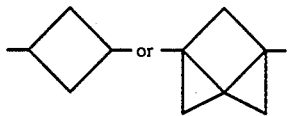

in such a manner that oxygen atoms are not linked directly to one another, r is 0 or 1, s is 0 or 1, Y is H or F, L is H or F, and W$_1$ is an alkyl or alkenyl radical having up to 15 C atoms, these radicals being unsubstituted or substituted by halogen, it also being possible for one or more CH$_2$ groups in these radicals to be replaced, in each case independently of one another, by —O—,

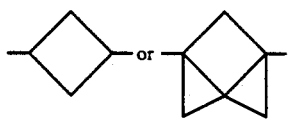

in such a manner that oxygen atoms are not linked directly to one another, or F, Cl, CF$_3$, OCF$_3$ or OCHF$_2$.

The liquid crystal mixture preferably comprises one or more compounds of the formula IV

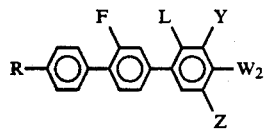    IV wherein

R is an alkyl or alkenyl radical having up to 15 C atoms, these radicals being unsubstituted or substituted by halogen, it also being possible for one or more CH$_2$ groups in these radicals to be replaced, in each case independently of one another, by —O—,

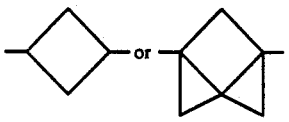

in such a marker that oxygen atoms are not linked directly to one another, L, Y and Z are each H or F, and W$_2$ is an alkyl or alkenyl radical having up to 15 C atoms, these radicals being unsubstituted or substituted by halogen, it also being possible for one or more CH$_2$ groups in these radicals to be replaced, in each case independently of one another, by —O—,

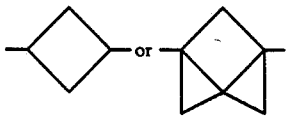

in such a manner that oxygen atoms are not linked directly to one another, or F, CF$_3$, OCF$_3$ or OCHF$_2$.

The liquid crystal mixture contains one or more compounds of the group consisting of III to IX

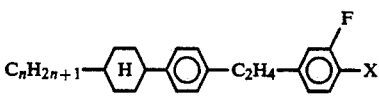    III'

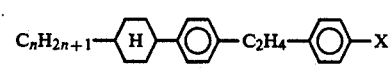    IV'

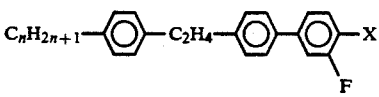    V'

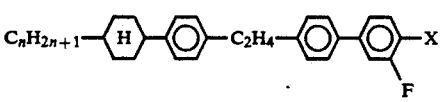    VI'

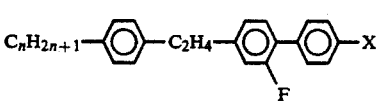    VII'

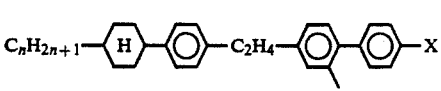    VIII'

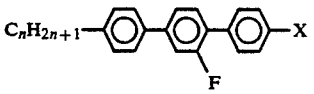    IX' wherein n is preferably 1 to 7 and X denotes F, Cl, CF$_3$, OCF$_3$ or OCHF$_2$. Preferred mixtures contain 10–65%, more preferably, 18–45% of formula II and/or 35–90, more preferably 55–85% by weight of compounds of formulae II–IX'.

Especially preferred are LC mixtures with one or more chloroterphenyls of formula I and less than 15%, preferably less than 10% of compounds of formulae 1 to 5 of EP 04 39 089 wherein R$^1$ and R$^2$ is selected from alkyl, alkenyl, alkoxy, alkenyloxy and alkanoyloxy.

The compounds shown above are known from e.g. DOS 30 42 391, DOS 39 02 328, DOS 39 13 554, DOS 39 09 802, WO 89/02884, WO 90/15113, WO90/09420, the International Patent Appln. No. PCT/EP 90/01292, No. PCT/EP 91/00411, No. PCT/EP 90/01471, No. PCT/EP 90/0 2109 and the European Patent Appln. No. 9 1 100 675.7 or can be prepared in analogy to known compounds.

The mixtures according to the present invention usually are based on the medium polar components having the indicated core structure and other non-cyano components. Of course, however, such mixtures can also additionally contain known cyano LC components if extremely high values for the HR are not needed, e.g. for TN or STN-use. Such mixtures can also contain tolan components for adjusting extremely high Δn values. The resulting mixtures are important for achieving very broad nematic phase ranges including very low temperatures (outdoor use).

The mixtures are preferably based on halogenated components of medium polarity and/or are essentially free of cyano components. Meant by medium polarity is a dielectric anisotropy Δε preferably in the range from 0.5 to +15.0. Essentially free of cyano components preferably means 10% by weight (preferably 5%) of cyano components.

The novel compounds of the formula Ia comprise those of the preferred part-formulae Ia1 to Ia3:

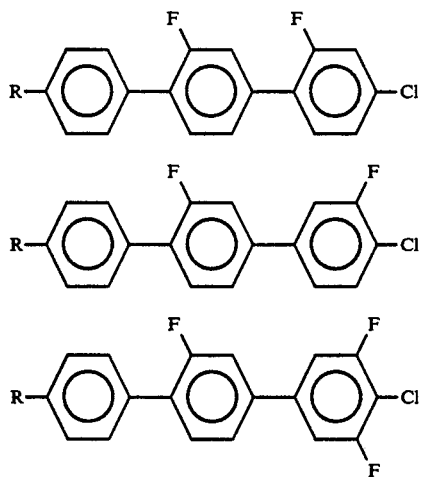

and can be prepared in analogy to the methods described in EP 0 439 089A1, WO 90/09420, WO 90/15113 and WO 91/13850, the disclosure of which is incorporated here by reference.

R is preferably a straight-chained alkyl radical of 1 to 7 carbon atoms or is straight-chained methoxy alkyl (methoxymethyl, methoxyalkyl, methoxypropyl, methoxybutyl, methoxypentyl, methoxyhexyl, methoxyheptyl).

The preparation of the mixtures according to the invention is effected in the conventional manner. In general, the desired amount of the components which is used in the smaller amount is dissolved in the components which constitutes the main constituent, preferably at elevated temperature. If this temperature is chosen to be above the clear point of the main constituent, the completeness of the process of dissolving can be observed particularly easily.

However, it is also possible to mix solutions of the components in a suitable organic solvent, for example acetone, chloroform or methanol, and to remove the solvent does not introduce any contaminants or undesirable dopants.

By means of suitable additives the liquid crystal phases according to the invention can be modified in such a way that they can be used in any hitherto disclosed kind of AMD.

Especially preferred are the mixtures of the present invention for use in active matrix projection systems including PDLC type systems.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications cited above, are hereby incorporated by reference.

The measurement of HR was performed as described by S. Matsumoto et al. (Liquid Crystals 5, 1320 (1989)) in standard 6 μ TN-displays without spacers. Standard floatglass with conductive ITO layers (Balzers) and a rubbed polyimide layer (AL-1051 of Japan Synthetic Rubber) as orientation layer was used. The cells were sealed with an UV-curable adhesive (NOA-61 of Norland) and filled under standard conditions. The liquid crystal mixture was composed of components being carefully purified under standard procedures. UV exposure was performed in a Heraeus-Suntest with a Xenon lamp (1.1 kw, 0.082 W/cm$^2$, UV cutoff 310 nm).

| | Holding Ratio Data (%) | | |
|---|---|---|---|
| Compound | Room Temp. | 1 hour 180° C. | 2 hours UV load |
| C$_5$H$_{11}$—⬡—⬡(F,F)—⬡—Cl | 98.4 | 98.4 | 98.3 |
| C$_3$H$_7$—⬡—⬡—⬡(F,F)—Cl | 98.6 | 98.6 | 98.3 |
| C$_5$H$_{11}$—⬡—⬡(F,F)—⬡—Cl | 98.6 | 98.6 | 97. |

All values are % age values, measured as 15% w/w solutions in ZLI 3086 which is a LC mixture commercially available from E. Merck, Darmstadt, Germany.

In the present patent application and in the following examples all chemical structures of LC compounds are given by acronyms the transformation of which into chemical formulae is done as shown in the following. All residues $C_nH_{2n+1}$ and $C_mH_{2m+1}$ are straight-chained alkyl groups with resp. n and m carbon atoms.

The code of Table B is self-explanatory. In Table A only the acronym for the core structure is given. In a specific formula, this acronym is followed by a dash and a code for the substituents $R^1$, $R^2$, $L^1$ and $L^2$ as follows:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nOmFF | $C_nH_{2n+1}$ | $OC_mH_{2m+1}$ | F | F |
| nmF | $C_nH_{2n+1}$ | $C_mH_{2m+1}$ | F | H |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}-CH=CH-C_sH_{2s}-$ | CN | H | H |
| rEsN | $C_rH_{24+1}-O-C_sH_{2s}-$ | CN | H | H |
| nNF | $C_nH_{2n+1}$ | CN | F | H |
| nAm | $C_nH_{2n+1}$ | $COOC_mH_{2m+1}$ | H | H |

TABLE A

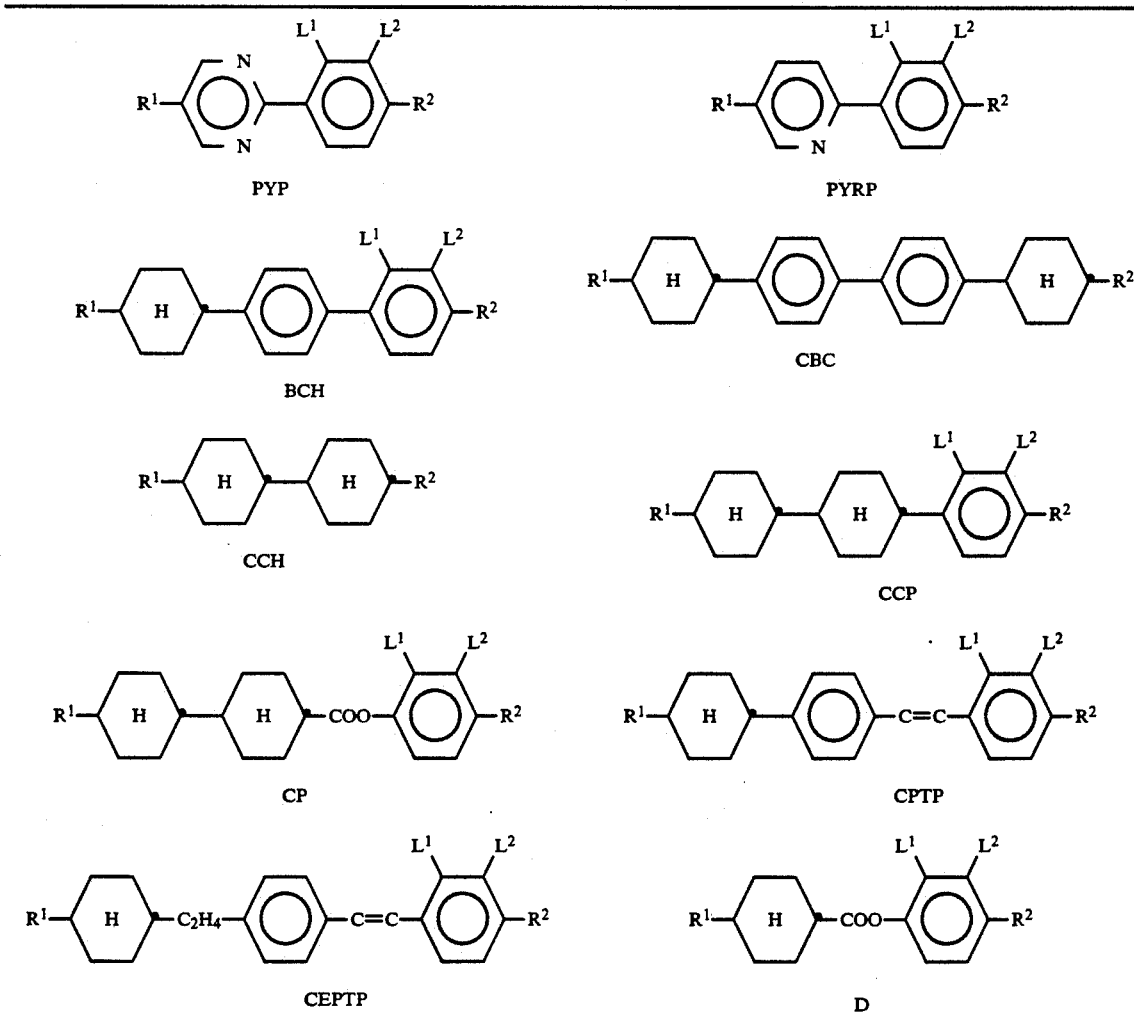

TABLE A-continued
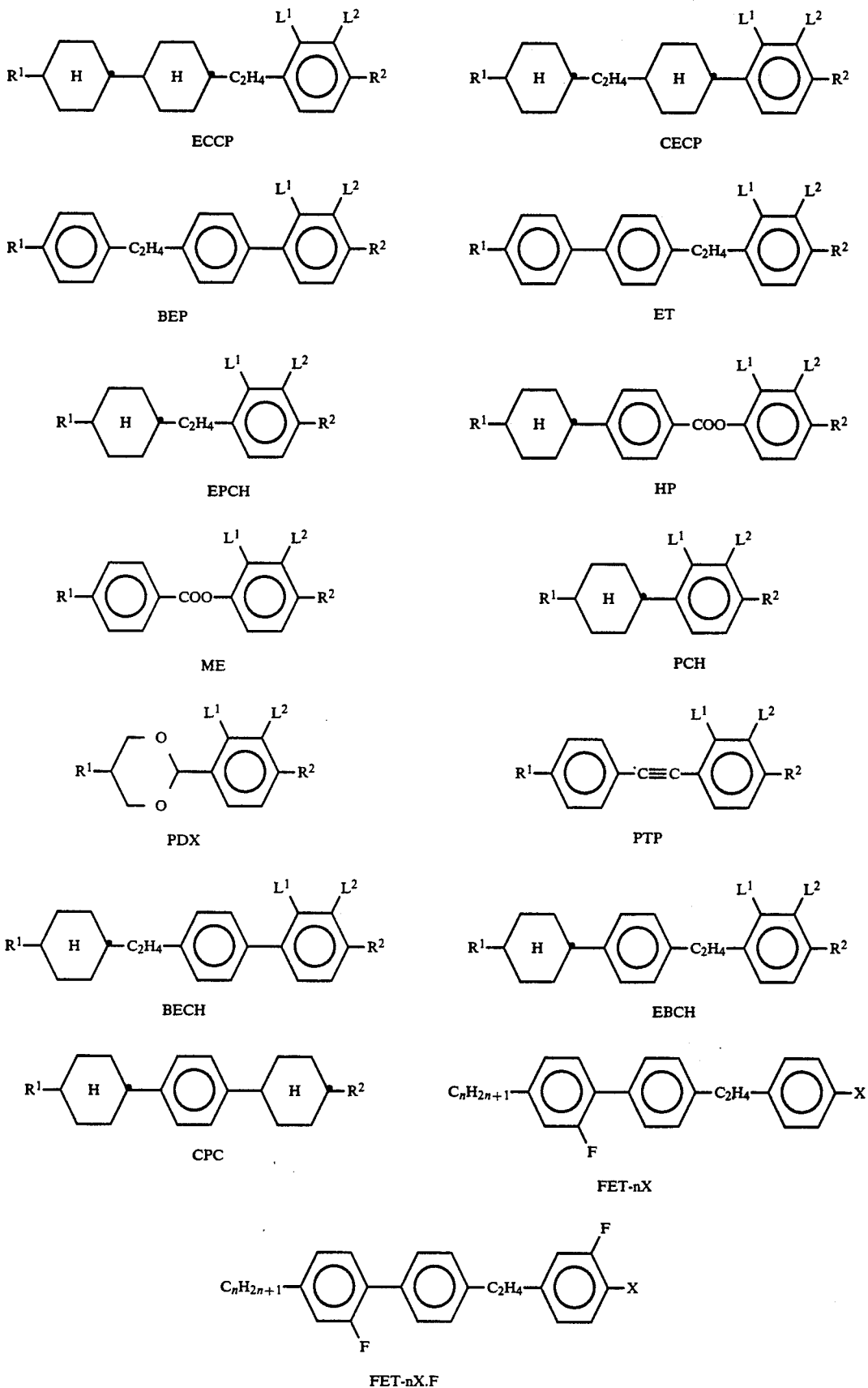

TABLE A-continued
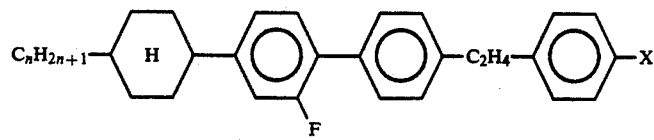
CFET-nX
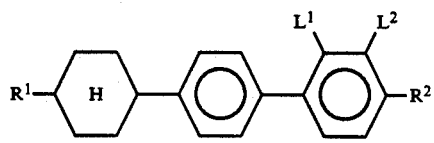
BCH
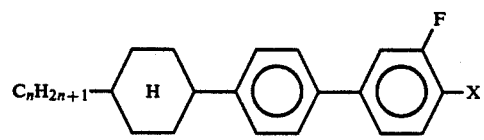
BCH-nX.F
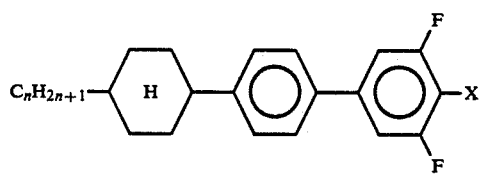
BCH-nX.F.F
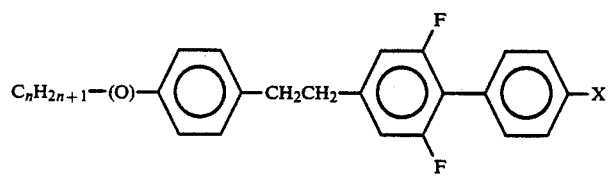
PEUP-n(O)X
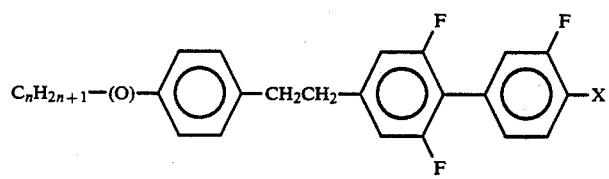
PEUP-n(O)X.F
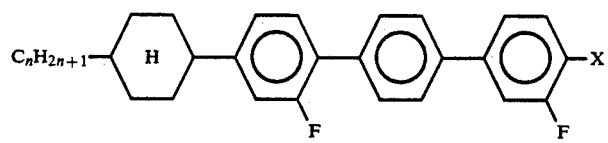
CLPP-nX.F
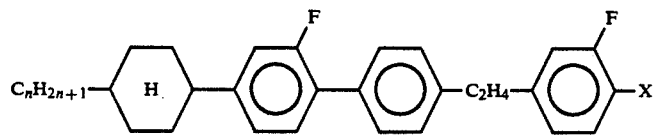
CFET-n.X.F
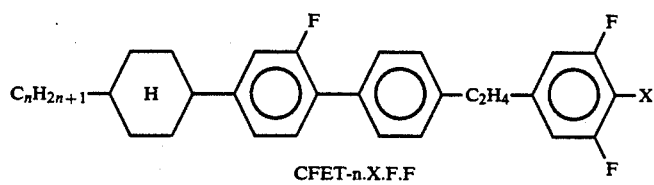
CFET-n.X.F.F

TABLE A-continued
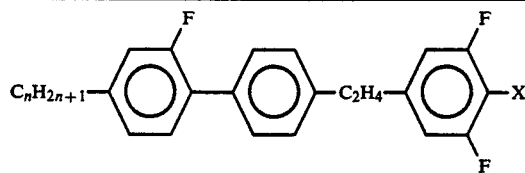
FET-nX.F.F
TABLE B
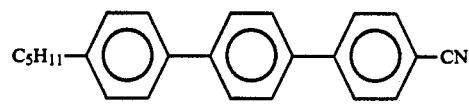
T15
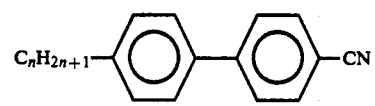
K3n
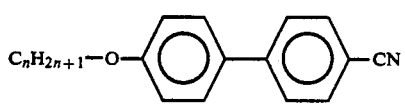
M3n
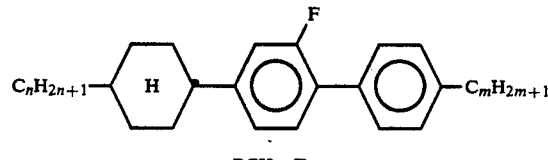
BCH-n.Fm
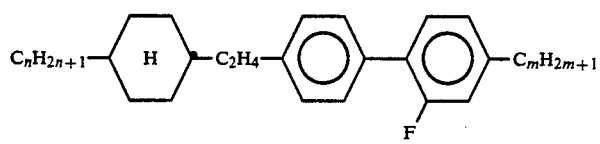
Inm
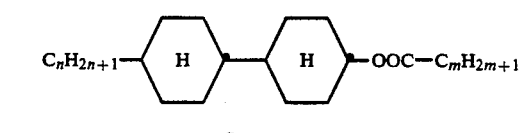
C-nm
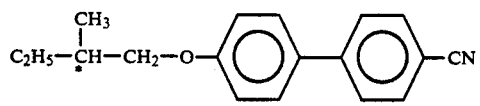
C15
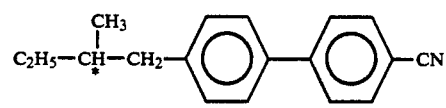
CB15
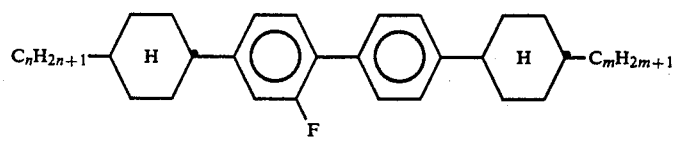
CBC-nmF
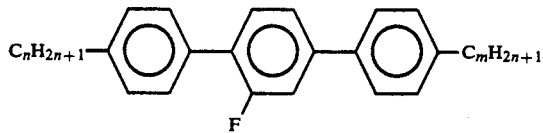
T-nFm
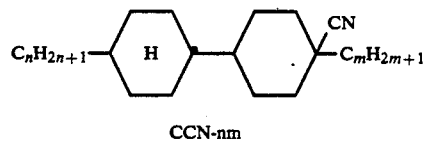
CCN-nm
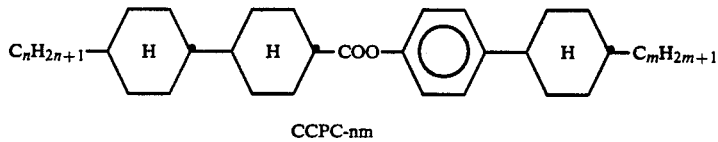
CCPC-nm TABLE B-continued
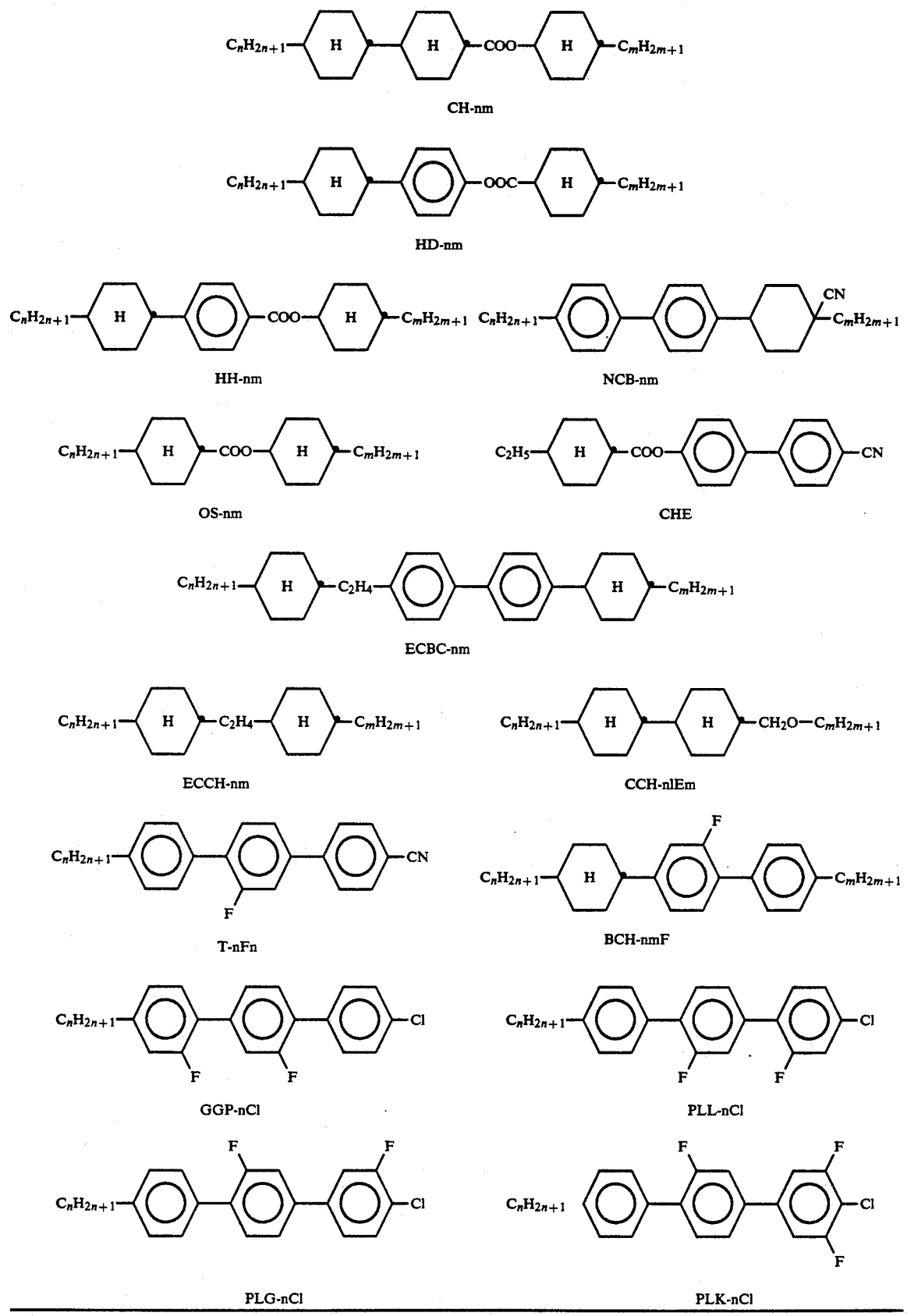

EXAMPLE 1

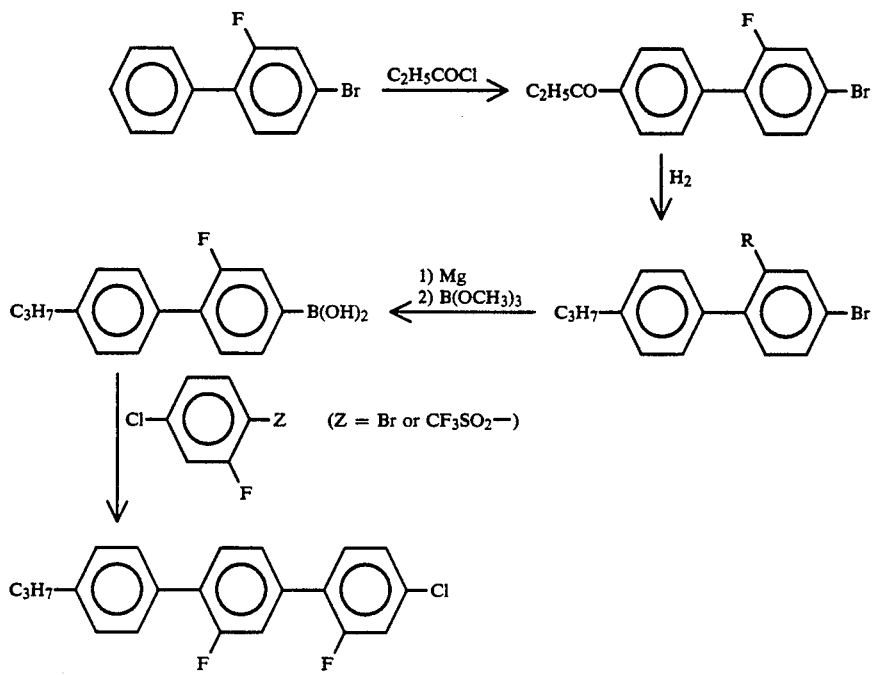

A mixture of 0.05 m of boronic acid and 0.05 m of the bromo-chloro-fluorobenzene in 100 ml of toluene and 40 ml of ethanol is reacted with 50 ml 2 m Na$_2$CO$_3$ solution with 1 g of tetrakis triphenylphosphine Pd-(O) catalyst. After 4 h heating under reflux the mixture is worked up by extraction. After chromatography and crystallization pure

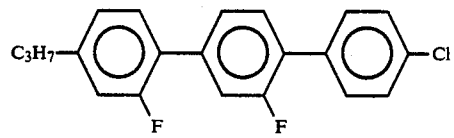

is obtained: C 75 N 105 I.

Analogously the following terphenyls are obtainable from corresponding (fluorinated) chlorophenyl boronic acids:

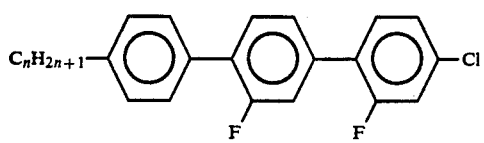

n = 2 C 104 I
4
5 C 68 N 105.5 I
7

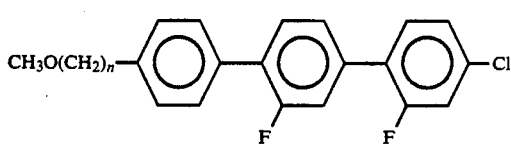

n = 1
2
3
4
5

C$_2$H$_{2n+1}$—[ring]—[ring(F)]—[ring(F)]—Cl n = 2
3 C 85 N 109.8 I
4
5 C 54 S 102 N 113 I
7

C$_2$H$_{2n+1}$—[ring]—[ring(F)]—[ring]—Cl n = 2
3 C 127 N 162.5 I
4
5 C 96 S 134 N 157.6 I
7

EXAMPLE 2

| | | |
|---|---|---|
| FET-2Cl | 18.2% | |
| FET-3Cl | 9.4% | |
| FET-5Cl | 29.4% | |
| BCH-32F | 5.0% | Clp. 88.3° |
| BCH-3F.F | 5.0% | nΔ 0.225 |
| PLL-3Cl | 8.0% | η$_{20}$ 53 cSt |
| PLG-3Cl | 7.0% | |
| GGP-3Cl | 8.0% | |
| GGP-5Cl | 10.0% | |

EXAMPLE 3

| FET-2Cl | 20.3% | |
| --- | --- | --- |
| FET-3Cl | 10.4% | Clp. 90.0° |
| FET-5Cl | 27.3% | Δn 0.233 |
| BCH-3F.F | 6.0% | η₂₀ 53 cST |
| CBC-33F | 3.0% | |
| PLL-3Cl | 8.0% | |
| PLG-3Cl | 7.0% | |
| GGP-3Cl | 8.0% | |
| GGP-5Cl | 10.0% | |

EXAMPLE 4

| FET-2Cl | 19.6% | |
| --- | --- | --- |
| FET-3Cl | 10.1% | |
| FET-5Cl | 26.3% | |
| GGP-5Cl | 12.0% | Clp. 92.7° |
| PLG-3Cl | 6.0% | Δn 0.222 |
| PLL-3Cl | 8.0% | |
| BCH-32F | 5.0% | |
| BCH-3F.F | 5.0% | |
| BCH-5F.F | 5.0% | |
| CBC-33F | 3.0 | |

EXAMPLE 5

| FET-2Cl | 19.6% | |
| --- | --- | --- |
| FET-3Cl | 10.1% | |
| FET-5Cl | 26.3% | Clp. 92.1° |
| BCH-32F | 5.0% | Δn 0.224 |
| BCH-3F.F | 5.0% | η₂₀ 50 cST |
| BCH-5F.F | 5.0% | |
| CBC-33F | 3.0% | |
| PLL-3Cl | 8.0% | |
| PLG-3Cl | 6.0% | |
| GGP-3Cl | 12.0% | |

EXAMPLE 6

| FET-2Cl | 22.4% | |
| --- | --- | --- |
| FET-3Cl | 11.5% | |
| FET-5Cl | 30.1% | Clp. 84.3° |
| GGP-5Cl | 12.0% | Δn 0.226 |
| PLG-3Cl | 6.0% | |
| PLL-3Cl | 8.0% | |
| BCH-3F.F | 5.0% | |
| BCH-5F.F | 5.0% | |

EXAMPLE 7

| FET-2Cl | 24.2% | |
| --- | --- | --- |
| FET-3Cl | 12.4% | Clp. 87.6° |
| FET-5Cl | 32.4% | |
| PLG-3Cl | 8.0% | Δn 0.222 |
| PLL-3Cl | 10.0% | |
| BCH-3F.F | 5.0% | |
| BCH-5F.F | 5.0% | |
| CBC-33F | | |

EXAMPLE 8

| FET-2Cl | 22.4% | |
| --- | --- | --- |
| FET-3Cl | 11.5% | |
| FET-5Cl | 30.1% | |
| BCH-32F | 5.0% | Clp. 90.2° |
| BCH-3F.F | 5.0% | Δn 0.216 |
| BCH-5F.F | 5.0% | η₂₀ 46 cST |
| CBC-33F | 3.0% | |
| GGP-3Cl | 8.0% | |
| GGP-5Cl | 10.0% | |

EXAMPLE 9

| FET-2Cl | 21.1% | |
| --- | --- | --- |
| FET-3Cl | 10.8% | Clp. 93.3° |
| FET-5Cl | 28.3% | Δn 0.222 |
| GGP-5Cl | 15.0% | |
| PLG-3Cl | 9.8% | |
| BCH-3F.F | 5.0% | |
| BCH-5F.F | 5.0% | |
| CBC-33F | 5.0% | |

EXAMPLE 10

| FET-2Cl | 19.6% | |
| --- | --- | --- |
| FET-3Cl | 10.1% | |
| FET-5Cl | 26.3% | |
| BCH-32F | 5.0% | Clp. 93° |
| BCH-3F.F | 5.0% | Δn 0.222 |
| BCH-5F.F | 5.0% | Δε +6.8 |
| CBC-33F | 3.0% | |
| GGP-5Cl | 12.0% | |
| PLG-3Cl | 6.0% | |
| PLL-3Cl | 8.0% | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A nematic liquid crystal mixture having a positive dielectric anisotropy Δε of at least one fluorinated chloroterphenyl compound of formula I, Ia1, Ia2 or Ia3:

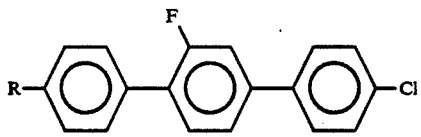

I

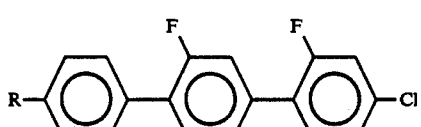

Ia1

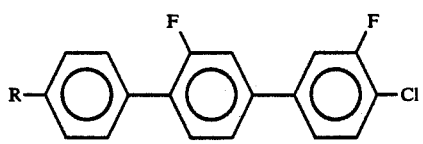

Ia2

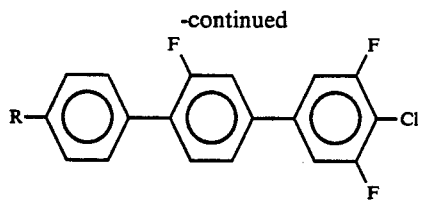

wherein
R is an alkyl or alkenyl radical having up to 15 C atoms, said radical being unsubstituted or substituted by halogen, one or more CH₂ groups in the radical optionally being replaced, in each case independently of one another, by —O—,

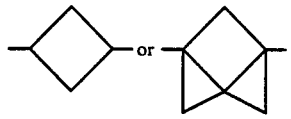

in such a manner that oxygen atoms are not linked directly to one another.

2. A mixture according to claim 1, comprising halogenated liquid crystal components of medium polarity.

3. A mixture according to claim 1, which is essentially free of cyano components.

4. A mixture according to claim 1, wherein the liquid crystal mixture further comprises at least one compound of formula II

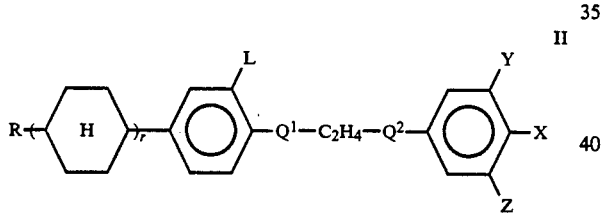

wherein
R is an alkyl or alkenyl radical having up to 15 C atoms, said radical being unsubstituted or substituted by halogen, one or more CH₂ groups in these radicals optionally being replaced, in each case independently of one another, by —O—,

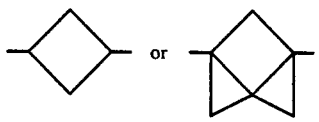

in such a manner that oxygen atoms are not linked directly to one another,
r is 0 or 1,
X is F, Cl, CF₃, OCF₃ or OCHF₂, and L, Y and Z are each H or F, and one of Q¹ and Q² is 1,4-phenylene or 3-fluoro-1,4-phenylene and the other is a single bond.

5. A mixture according to claim 1, wherein the liquid crystal mixture further comprises at least one compound of formula III

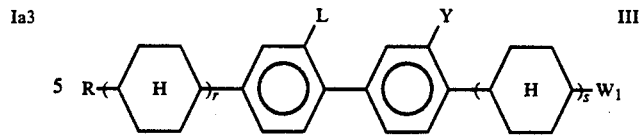

wherein
R is an alkyl or alkenyl radical having up to 15 C atoms, said radical being unsubstituted or substituted by halogen, one or more CH₂ groups in the radical optionally being replaced, in each case independently of one another, by —O—

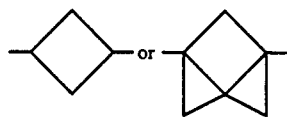

in such a manner that oxygen atoms are not linked directly to one another,
r is 0 or 1,
s is 0 or 1,
Y is H or F,
L is H or F, and
W₁ is an alkyl or alkenyl radical having up to 15 C atoms, said radical being unsubstituted or substituted by halogen, one or more CH₂ groups in the radical optionally being replaced, in each case independently of one another, by —O—,

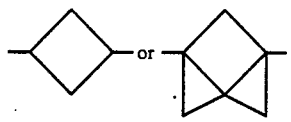

in such a manner that oxygen atoms are not linked directly to one another, or F, Cl, CF₃, OCF₃ or OCHF₂.

6. A mixture according to claim 1, wherein the liquid crystal mixture comprises at least one compound of formula IV

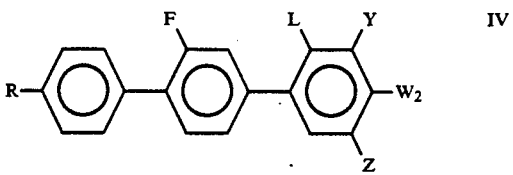

wherein
R is an alkyl or alkenyl radical having up to 15 C atoms, said radical being unsubstituted or substituted by halogen, one or more CH₂ groups in the radical optionally being replaced, in each case independently of one another, by —O—

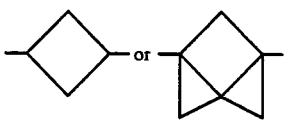

in such a manner that oxygen atoms are not linked directly to one another,

L, Y and Z are each independently H or F, and $W_2$ is an alkyl or alkenyl radical having up to 15 C atoms, the radical being unsubstituted or substituted by halogen, one or more $CH_2$ groups in the radical optionally being replaced, in each case independently of one another, by —O—,

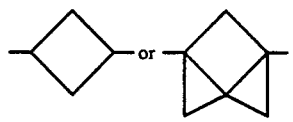

in such a manner that oxygen atoms are not linked directly to one another, or F, $CF_3$, $OCF_3$ or $OCHF_2$.

7. A fluorinated chloroterphenyl of formula Ia

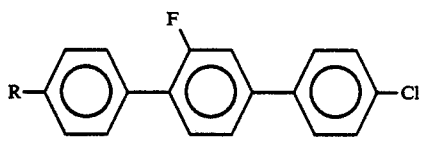

wherein

R is an alkyl or alkenyl radical having up to 15 C atoms, the radical being unsubstituted or substituted by halogen, one or more $CH_2$ groups in these radicals optionally being replaced, in each case independently of one another, by —O—,

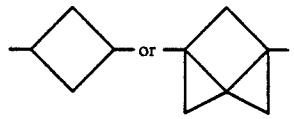

in such manner that oxygen atoms are not linked directly to one another.

8. A fluorinated chloroterphenyl of the formula IA1:

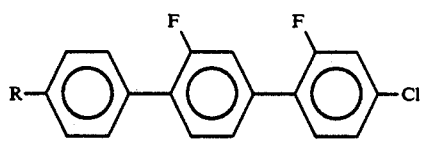

wherein

R is an alkyl or alkenyl radical having up to 15 C atoms, the radical being unsubstituted or substituted by halogen, one or more $CH_2$ groups in these radicals optionally being replaced, in each case independently of one another, by —O—,

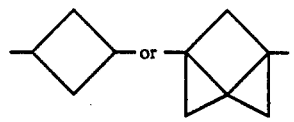

in such manner that oxygen atoms are not linked directly to one another.

9. A fluorinated chloroterphenyl of the formula Ia2:

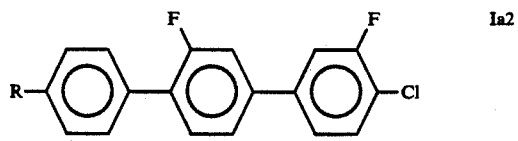

wherein

R is an alkyl or alkenyl radical having up to 15 C atoms, the radical being unsubstituted or substituted by halogen, one or more $CH_2$ groups in these radicals optionally being replaced, in each case independently of one another, by —O—,

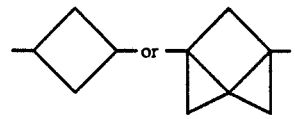

in such manner that oxygen atoms are not linked directly to one another.

10. A fluorinated chloroterphenyl of the formula Ia3:

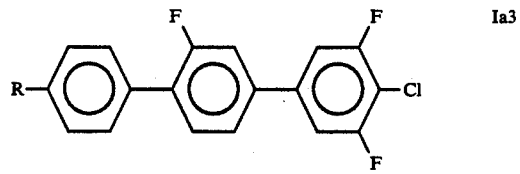

wherein

R is an alkyl or alkenyl radical having up to 15 C atoms, the radical being unsubstituted or substituted by halogen, one or more $CH_2$ groups in these radicals optionally being replaced, in each case independently of one another, by —O—,

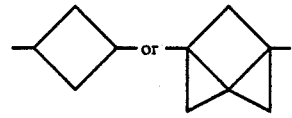

in such manner that oxygen atoms are not linked directly to one another.

* * * * *